United States Patent [19]

Haas et al.

[11] 4,000,144

[45] Dec. 28, 1976

[54] ADAMANTYL-PHENYLTHIOALKANE DERIVATIVES

[75] Inventors: Georges Haas, Oberwil; Roland Jaques, Allschwil; Alberto Rossi, Oberwil; Martin Rüegg, Fullinsdorf, all of Switzerland

[73] Assignee: Ciba-Geigy Corporation, Ardsley, N.Y.

[22] Filed: Aug. 18, 1975

[21] Appl. No.: 605,571

Related U.S. Application Data

[62] Division of Ser. No. 409,192, Oct. 24, 1973, Pat. No. 3,933,835.

[30] Foreign Application Priority Data

Nov. 1, 1972 Switzerland .................. 15923/72
Sept. 18, 1973 Switzerland .................. 13386/73

[52] U.S. Cl. .................. 260/294.8 B; 260/295 T; 260/295.5 T; 260/470; 260/515 M; 260/516; 260/481 R; 424/263; 424/308; 424/309
[51] Int. Cl.$^2$ ...................................... C07D 213/55
[58] Field of Search .............. 260/295.5 R, 295 T, 260/294.8 B, 515 M, 516, 481 R, 470, 612 D, 295.5 T

[56] References Cited

UNITED STATES PATENTS 3,928,363  12/1975  Haas et al. .................. 260/295.5 R

*Primary Examiner*—Alan L. Rotman
*Attorney, Agent, or Firm*—Joseph G. Kolodny; Theodore O. Groeger; John J. Maitner

[57] ABSTRACT

Compounds of the formula I $$R_1 - Ph - X - alk - R_2 \quad (I)$$

wherein $R_1$ is adamantyl, Ph is phenylene which is optionally substituted by amino, nitro, lower alkyl, lower alkoxy, halogen or trifluoromethyl, X is oxy or thio, alk is alkylene with 1 to 20 C atoms or alkenylene with 2 to 20 C atoms and $R_2$ is free, esterified or amidised carboxyl, sulpho or sulphonamido and therapeutically acceptable salts thereof are useful as anti-allergic and hypolipidaemic agents.

6 Claims, No Drawings

ADAMANTYL-PHENYLTHIOALKANE DERIVATIVES

This is a division of application Ser. No. 409,192, filed Oct. 24, 1973, now U.S. Pat. No. 3,933,835.

The invention relates to new compounds of the general formula I

 (I)

wherein $R_1$ represents an aliphatic tricyclic or tetracyclic hydrocarbon radical, $R_2$ is optionally functionally modified carboxyl, sulpho or sulphonamido, Ph is optionally substituted phenylene, X is oxy, thio, sulphinyl or sulphonyl and alk is alkylene or alkenylene, and processes for their manufacture.

Lower radicals hereafter denote radicals with up to 8, preferably with up to 4, C atoms.

Aliphatic radicals are radicals whereof the free valency extends from a C atom which is not a member of aromatic system.

Aliphatic, tricyclic or tetracyclic hydrocarbon radicals $R_1$, which can also be lower-alkylated, are, for example, unsaturated or above all saturated, such as radicals of the general formula $C_mH_{(2m-y)}$, wherein $n$ denotes the numbers 8 to 15 and $y$ can be 5, 7, 9 or 11, such as 1- or 2-adamantyl, homoadamantyl, for example 1-homoadamantyl, octahydro-1,2,4-methenopentalenyl, twistanyl or bullvalenyl.

Optionally functionally modified carboxyl groups $R_2$ are, for example, the nitrile group, amidino group or hydroxyaminocarbonyl group, amidised carboxyl groups or, in particular, free or esterified carboxyl groups.

Esterified carboxyl groups are in particular those esterified with aliphatic, cycloaliphatic or araliphatic alcohols. Ester-forming alcohols which have been used are, in particular, lower alkanols which contain up to 7 C atoms and can be straight-chain or branched chain, such as, for example, methanol, ethanol, n-propanol, isopropanol, butanols, hexanols or heptanols, cycloalkanols which contain 4 to 8 C atoms, preferably 5 or 6 C atoms, in the ring and which can be substituted by lower alkyl such as, for example, cyclopentanol or cyclohexanol, phenyl-lower alkanols, of which the phenyl radical is unsubstituted or can contain one or more substituents, such as lower alkyl, lower alkoxy, halogen or trifluoromethyl, and of which the lower alkanol part has the abovementioned meaning, for example benzyl alcohol or 2-phenylethanol, or alcohols of the formula HO-Q-Py, wherein Q denotes an alkylene radical or a direct bond and Py denotes a pyridyl radical. Alkylene radicals Y are straight-chain or branched chain lower alkylene radicals with 1 to 3 C atoms in the alkylene chain, preferably those with a total of 1 to 4 C atoms, such as, above all, 1,3- or 1,2-propylene or especially propylidene, isopropylidene, ethylidene, ethylene or methylene.

In the amidised carboxyl groups (carbamoyl groups), the amide nitrogen atom can be unsubstituted, monosubstituted or disubstituted, for example by preferably lower radicals, for example radicals possessing at most 8 carbon atoms, of aliphatic character, which can also be interrupted by heteroatoms, such as oxygen atoms or sulphur atoms.

As examples of amide substituents there may be mentioned alkyl, alkenyl or alkylene radicals which can also be interrupted by oxygen or sulphur atoms, and also phenylalkyl.

Possible amide substituents are in particular: Lower alkyl radicals, such as methyl, ethyl, n-propyl, isopropyl or straight or branched butyl, pentyl, hexyl or heptyl bonded in any desired position, lower alkenyl radicals, such as, for example, allyl or methallyl, lower alkylene radicals such as, for example, butylene-(1,4), pentylene-(1,5), hexylene-(1,6) or heptylene-(2,6), or corresponding radicals interrupted by the hetero-atoms mentioned, such as, for example, lower alkoxyalkyl or alkylmercaptoalkyl radicals, such as, for example, 2-methoxyethyl, 2-ethoxyethyl, 3-methoxypropyl or 2-methylmercaptoethyl, or oxaalkylene or thiaalkylene radicals, such as 3-oxa- or 3-thia-pentylene-(1,5) or 1,5-dimethyl-3-thiapentylene-(1,5), or phenylalkyl radicals, especially phenyl-lower alkyl radicals, which can be unsubstituted or monosubstituted or polysubstituted in the phenyl part, possible substituents being above all lower alkyl, lower alkoxy, halogen or trifluoromethyl, such as benzyl or 2-phenylethyl.

The amino group of the amidised carboxyl group (carbamoyl group) is in particular a free, mono- or di-lower alkylated amino group, or an optionally C-lower alkylated pyrrolidino, piperidino, morpholino or thiomorpholino group.

Alkoxy radicals are above all lower alkoxy radicals, for example methoxy, ethoxy, propoxy, isopropoxy, butoxy, or amyloxy groups, and possible halogen atoms are above all fluorine, chlorine or bromine atoms.

A sulphonamido group is preferably a sulphonamido group which is monosubstituted by lower alkyl or phenyl-lower alkyl, with lower alkyl and phenyl-lower alkyl having the above meaning, for example the N-methylsulphonamido, N-ethylsulphonamido, N-benzylsulphonamido or N-(α-phenethyl)-sulphonamido group, it being possible for phenyl groups which may be present to be unsubstituted or monosubstituted or polysubstituted, possible substituents being lower alkyl, lower alkoxy, halogen or trifluoromethyl. The sulphamoyl group should be singled out particularly as a sulphonamido group.

The phenylene radicals Ph are o-, m- or preferably p-phenylene radicals.

The phenylene radicals pH can be unsubstituted or carry one, two or more substituents. Examples of possible substituents are the following: Alkyl radicals, such as lower alkyl radicals, alkoxy radicals, halogen atoms, especially those mentioned above, or trifluoromethyl radicals and nitro groups.

Alkylene alk in particular has 1 to 20 C atoms with a straight or branched chain. An optionally present side chain is preferably in the α-position to $R_2$. Unbranched alkylene radicals with 1 to 10 C atoms, above all with 1 to 4 C atoms, and radicals which carry an unbranched alkyl radical with 1 to 8 C atoms, especially methyl, in the α-position to $R_2$, are preferred. Examples which may be mentioned are methylene, 1,2-ethylene, 1,1-ethylene, 1,3-propylene, 1,4-butylene and 1,10-decylene.

Alkenylene in particular has 2 to 20, above all 2 to 7, C atoms and is straight-chain or branched chain. A side chain which is optionally present is preferably in the α- or β-position to $R_2$. Unbranched alkylene radicals with 2 or 3 C atoms, and radicals which carry an unbranched alkyl radical with 1 to 3 C atoms in the α-position or in the β-position to $R_2$, such a vinylene, 1,3-propenylene, 1,2-propenylene, 1,2-but-1-enylene and 1,2-but-2-enylene are preferred.

The new substances possess valuable pharmcological properties, above all an inhibiting action on the liberation of histamine, as is found in vitro in doses of about 0.003 to 0.015 mg/ml in the histamine liberation test on peritoneal cell suspensions of rats using [D-Ser$^1$, Lys$^{17,18}$]-α-corticotropine-(1-19)-nonadecapeptide-tetradecyl ester-hexaacetate [R. Jaques and M. Brugger, Pharmacology 2, 361–370, (1969); M. Brugger, Helv. chim. acta 54, 1261–1274, (1971)].

They are therefore useful as anti-allergy agents.

Furthermore, they show, for example, on peroral administration, in particular a hypolipidaemic activity which can be demonstrated, using standard methods, by, for example, the lowering of the cholesterol level and above all of the triglyceride level in the blood after repeated administration in doses of 30 mg/kg per day to male rats. The serum lipids are extracted according to J. Folch et al [compare J. Biol. Chem. 226, 497, (1951)] and the triglycerides are determined according to G. Kessler and H. Lederer [compare Automaticen in der Analytischen Chemie (1965); Technicon GMH, Frankfurt/Main, pages 863–872] and the total cholesterol according to W. D. Block et al [compare ibid., pages 970–971] on an autoanalyser.

The new substance are therefore useful as hypolipidaemic agents.

However, the new compounds are also valuable intermediate products for the manufacture of other useful substances, especially of pharmacologically active compounds.

Valuable compounds are above all compounds Ia of the formula I, wherein $R_1$ is adamantyl, Ph, alk and X have the above meaning and $R_2'$ represents a free, esterified or amidised carboxyl group, the sulpho group or a sulphonamido group.

Important compounds are above all compounds Ib of the formula I, wherein $R_1$ is adamantyl, Ph is phenylene which is optionally substituted by amino, nitro, lower alkyl, lower alkoxy, halogen or trifluoromethyl, X is oxy or thio, alk is alkylene with 1 to 20 C atoms or alkenylene with 2 to 20 C atoms and $R_2$ is free, esterified or amidised carboxyl, sulpho or sulphonamido.

Compounds which warrant particular mention are compounds Ic of the formula I, wherein $R_1$ is adamantyl, Ph is phenylene which is optionally substituted by amino, nitro, lower alkyl, lower alkoxy, halogen or trifluoromethyl, X is oxy or thio, alk is unbranched alkylene with 1 to 10 C atoms which optionally carries an unbranched alkyl radical with 1–8 C atoms in the α-position to $R_2$, or unbranched alkenylene with 2 to 7 C atoms which optionally carries an unbranched alkyl radical with 1 to 3 C atoms in the α- or β-position to $R_2$, and $R_2$ is carboxyl, lower alkoxycarbonyl, pyridyloxycarbonyl, pyridylmethoxycarbonyl, carbamoyl, nitrile or sulpho.

However, compounds to be singled out are above all compounds Id of the formula I, wherein $R_1$ is adamantyl, Ph is 1,4-phenylene, X is oxy, alk is -(CH$_2$)$_n$-CH(R$_3$)-, wherein $n$ is 0, 1 or 2, and $R_3$ is hydrogen or straight-chain alkyl with 1 to 8 C atoms, and $R_2$ is carboxyl, methoxycarbonyl, ethoxycarbonyl, pyridylmethoxycarbonyl or sulpho.

Compounds to be singled out particularly are compounds Ie of the formula I, wherein $R_1$ is adamantyl, Ph is 1,2- or especially 1,4-phenylene optionally substituted by amino, nitro, methoxy, methyl or chlorine, X is thio or especially oxy, alk is unbranched alkylene with 1–4 C atoms which can carry unbranched alkyl with 1 to 8 C atoms, especially methyl or n-octyl, in the α-position to $R_2$, or is unbranched alkenylene with 2 or 3 C atoms which can carry unbranched alkyl with 1 to 3 C atoms in the α- or β-position to $R_2$, and $R_2$ is carboxyl, $C_1$-$C_4$-alkoxycarbonyl, pyridyloxycarbonyl, pyridylmethoxycarbonyl, carbamoyl or sulpho.

The invention is particularly directed towards compounds If of the formula I, wherein $R_1$ is adamantyl, Ph is 1,4-phenylene, X is oxy, alk is unbranched alkylene with 1 to 4 C atoms which can carry methyl or n-octyl in the α-position to $R_2$, or unbranched alkenylene with 2 or 3 C atoms which can carry methyl or n-propyl in the α- or β-position to $R_2$, and $R_2$ is carboxyl, $C_1$-$C_3$-alkoxycarbonyl, pyridyloxycarbonyl, pyridylmethoxycarbonyl or sulpho, and very particularly the compounds mentioned in the examples.

The new compounds can be manufactured according to methods which are in themselves known.

For example, the compounds of the formula I are manufactured by reacting a compound of the formula II $$R_1 - Ph - X' \qquad\qquad II$$

wherein $R_1$ and Ph have the above meaning, and $X'$ represents a free hydroxyl or mercapto group, with a compound of the formula III $$Z - alk - R_2$$

wherein alk and $R_2$ have the above meaning and Z represents a reactive esterified hydroxyl group. This yields compounds of the formula I wherein X is oxy or thio.

A reactive esterified hydroxyl group is in particular a hydroxyl group esterified with a strong acid, such as a strong mineral acid, especially a hydrogen halide acid, for example hydrochloric acid or above all hydrobromic acid, or sulphuric acid, or with a strong organic acid, for example a sulphonic acid, such as a lower alkanesulphonic acid or bunzenesulphonic acid, for example methanesulphonic acid, ethanesulphonic acid or p-toluenesulphonic acid, or is a hydroxyl group which is esterified by the radical $R_2$, representing the sulpho group, to give a sultone. If a hydroxyl group of the acid component $R_2$ is esterified or amidised, a phenol or thiophenol II can preferably be employed as a salt, especially a metal salt, above all an alkali metal salt, for example a sodium salt or potassium salt. A preferred embodiment consists, for example, of reacting a suitable α-bromo-ester III with the sodium salt of a corresponding phenol or thiophenol II. The reaction can be carried out in the usual manner, especially in an inert, preferably anhydrous, solvent, and/or at elevated temperature, and/or in the presence of a strong base, for example an alkanolate, above all an alkali metal alkanolate, such as sodium alkanolate or potassium alkanolate, for example sodium ethanolate or sodium methanolate.

The new compounds are also obtained if a compound of the formula IV $$R_1 - Ph - X - alk - Z_1 \qquad\qquad IV$$

wherein $R_1$, Ph, X and alk have the above meaning, and $Z_1$ is a reactive esterified hydroxyl group, such as halogen, for example bromine, is reacted with a compound of the formula V $$u - R_2 \qquad\qquad V$$

wherein $R_2$ is, for example, the nitrile group, the sulpho group or the sulphonamido group and u denotes a metal, especially an alkali metal, for example sodium. The reaction is carried out in the usual manner, especially by heating a mixture of the components, preferably in a suitable solvent, for example in dimethylformamide.

In resulting compounds, substituents can be introduced, modified or split off within the scope of the end products.

Thus it is possible, for example, in resulting compounds wherein $R_2$ represents an optionally functionally modified carboxyl group, such as, for example, a free, amidised or esterified carboxyl group, or the nitrile, amidino or hydroxyaminocarbonyl group, to convert the radicals $R_2$ into one another.

Esterified carboxyl groups and amidised carboxyl groups, that is to say carbamoyl groups or nitrile, amidino or hydroxyaminocarbonyl groups, can be converted into free carboxyl groups in the usual manner, for example by hydrolysis, preferably in the presence of strong bases or strong acids, for example those mentioned above. If desired, oxidising agents, such as nitrous acid, can be added when hydrolysing carbamoyl groups.

Free or esterified carboxyl groups can also be converted into carbamoyl groups in the usual manner, for example by reaction with ammonia or amines possessing at least one hydrogen atom on the nitrogen atom, and, if appropriate, dehydration of the ammonium salt produced as an intermediate, for example with phosphorus pentoxide.

Unsubstituted carbamoyl groups can be converted into nitrile groups in the usual manner, for example by dehydration, preferably with phosphorus pentoxide.

Free carboxyl groups can be esterified in the usual manner, for example by reaction with an appropriate alcohol, advantageously in the presence of an acid, such as a mineral acid, for example sulphuric acid or hydrochloric acid, or in the presence of a water-binding agent, such as dicyclohexylcarbodiimide, or by reaction with an appropriate diazo compound, for example a diazoalkane. The esterification can also be carried out by reaction of a salt of the acid, for example of the sodium salt, with a reactively esterified alcohol, for example a halide, such as a chloride.

Free carboxyl groups can, for example, also be converted into acid halide groupings or acid anhydride groupings in the usual manner, for example by reaction with halides of phosphorus or sulphur, such as thionyl chloride, phosphorus pentachloride or phosphorus tribromide, or with acid halides, such as chloroformic acid esters. The acid anhydride groups or acid halide groups can then be converted into esterified carboxyl groups or carbamoyl groups in the usual manner, by reaction with appropriate alcohols, if desired in the presence of acid-binding agents, such as organic or inorganic bases, or by reaction with ammonia or amines.

Furthermore, sulpho groups and sulphonamido groups, for example lower alkyl-monosubstituted sulphonamido groups, can be converted into one another in resulting compounds.

The free sulphonamido group can be monoalkylated in a manner which is in itself known, for example with reactive esterified lower alkanols, such as halogeno-lower alkanes, or with di-lower alkyl sulphate, such as dimethyl sulphate, preferably in the presence of strong bases, for example sodium hydroxide.

Furthermore it is possible, in resulting compounds wherein Ph represents a substituted or unsubstituted phenylene radical, to introduce, convert or remove substituents of Ph.

Thus, halogenation, such as chlorination or bromination, can be carried out in the usual manner, for example with free chlorine or bromine, without or, preferably, with catalysts, such as, for example, iron-III chloride, or with N-chlorosuccinimide.

On the other hand, halogen, for example bromine, which is present can be removed hydrogenolytically, for example with hydrogen in the presence of a catalyst, such as palladium or Raney nickel, or with triethyl-tin hydride.

Equally, nitro groups can be introduced in the usual manner, especially by nitration, for example with a mixture of nitric acid and sulphuric acid.

Furthermore, trifluoromethyl groups can be introduced into a radical Ph, for example with trifluoromethyl iodide, using copper powder.

Further, resulting compounds of the formula I which carry at least one hydrogen atom in the $\alpha$-position to $R_2$ can be $\alpha$-alkylated, especially by reaction with a reactively esterified lower alkanol, such as a lower alkyl halide, for example methyl iodide or 1-n-octyl bromide, in which reaction metallisation is first carried out, that is to say the $\alpha$-hydrogen atom is replaced by a metal, such as an alkali metal, for example sodium or lithium, in the usual manner, using, for example, metal hydrides, amides or alkyls, preferably alkali metal hydrides, amides or alkyls, for example sodium amide, sodium hydride, lithium N,N-di-isopropylamide or butyl-lithium, as metallising agents.

Resulting compounds wherein X represents sulphur can be oxidised to the S-oxides (sulphoxides) or S-dioxides (sulphones).

The oxidation to the sulphoxides or sulphones can be carried out in a manner which is in itself known, for example by reaction with an S-oxidising agent, such as hydrogen peroxide, per-acids, especially peracetic acid, perbenzoic acid or monoperphthalic acids, which can also be substituted, for example by halogen atoms, chromic acid, potassium permanganate, hypohalites or nitric acid, nitrous gases and the like, or electrolytically. In these reactions the sulphoxides are obtained at lower temperatures, especially with good cooling, or when using only one mol equivalent of the oxidising agent, whilst on warming and/or using at least 2 mol equivalents of the oxidising agent the sulphones are obtained.

Resulting S-oxides can be oxidised to the S-dioxides. This oxidation can be carried out in a manner which is in itself known, for example as in the case of the oxidation described above which leads to the dioxides.

Resulting S-oxides can be reduced to the corresponding S-unsubstituted compounds of the formula I, for example with a reducing agent, such as nascent hydrogen, for example zinc and mineral acid, such as hydrochloric acid, or, for example, with sulphites or hydriodic acid.

In resulting compounds, alkenylene radicals alk can be converted into alkylene radicals alk, especially by hydrogen in the presence of a catalyst, such as a heavy metal catalyst, for example palladium or platinum. An isomerisation of a double bond can also take place on a catalyst, especially on a hydrogenation catalyst; for example, β-γ-unsaturated compounds can be obtained from α-β-unsaturated compounds.

In the above reductions care must be taken, where appropriate, that further reducible groups are not attacked. Thus it is particularly necessary to take care, in the case of the reduction with Raney nickel and hydrogen, that halogen atoms which may be present and are bonded to aromatic rings are not replaced by hydrogen. In addition, care must be taken with a thioether grouping in all reductions, especially catalytic hydrogenations. Preferably, sulphur-resistant catalysts should be used and where necessary the hydrogen absorption must be followed volumetrically and the hydrogenation stopped after the calculated amount has been absorbed.

The reactions mentioned can optionally be carried out simultaneously or successively and in optional sequence.

The reactions mentioned are carried out in the usual manner in the presence or absence of diluents, condensation agents and/or catalytic agents, at lowered, ordinary or elevated temperature and in a closed vessel if appropriate.

The invention also relates to those embodiments of the process according to which a compound obtainable as an intermediate product at any stage of the process is used as the starting compound and the missing process steps are carried out, or the process is stopped at any stage, or a starting substance is formed under the reaction conditions, or one reaction component is optionally present in the form of its salts.

Depending on the process conditions and starting substances, end products which may be salt-forming are obtained in the free form or in the form of their salts which can be converted into one another, or into other salts, in the usual manner. Thus acid end products, for example end products in which a free carboxyl group or the sulpho group is present, are obtained in the free form or in the form of their salts with bases. Resulting free acid compounds can be converted in the usual manner, for example by reaction with appropriate basic agents, into the salts with bases, above all into therapeutically usable salts with bases, for example salts with organic amines, or metal salts. Possible metal salts are, above all, alkali metal salts or alkaline earth metal salts, such as sodium, potassium, magnesium or calcium salts. Free acids can be liberated from the salts in the usual manner, for example by reaction with acid agents.

These and other salts can also be used for the purification of the new compounds, for example by converting the free compounds into their salts, isolating these and reconverting them into the free compounds. Because of the close relationships between the new compounds in the free form and in the form of their salts, the free compounds are to be understood, in the preceding and following text, where appropriate also to include the corresponding salts, as regards general sense and intended use.

The new compounds can, depending on the choice of the starting substances and procedures, and depending on the number of asymmetrical carbon atoms, be in the form of optical antipodes, racemates or isomer mixtures.

Isomer mixtures obtained can be separated into the two stereoisomeric (diastereomeric) pure isomers on the basis of the physico-chemical differences of the constituents, in a known manner, for example by chromatography and/or fractional crystallisation.

Racemates obtained can be resolved into the optical antipodes according to known methods, for example by recrystallisation from an optically active solvent, with the aid of micro-organisms or by reaction of a free carboxylic acid with an optically active base which forms salts with the racemic compound and separation of the salts obtained in this manner, for example on the basis of their differing solubilities, into the diastereomers; the antipodes can then be liberated from the latter by the action of suitable agents. Particularly customary optically active bases are, for example, (−)-brucine, (+)-quinidine, (−)-quinine, (+)-cinchonine, (+)-dehydroabietylamine, (+)- and (−)-ephedrine, (+)- and (−)-1-phenyl-ethylamine or their N-monoalkylated or dialkylated derivatives. Advantageously, the more active of the two antipodes is isolated.

The new compounds can be used, for example, in the form of pharmaceutical preparations in which they are present in the free form or optionally in the form of their salts, especially of the therapeutically usable alkali metal salts, mixed with a pharmaceutical, organic or inorganic, solid or liquid excipient suitable, for example, for enteral or parenteral administration. Possible substances for forming the excipient are those which do not react with the new compounds such as, for example, water, gelatine, lactose, starch, stearyl alcohol, magnesium stearate, talc, vegetable oils, benzyl alcohol, propylene glycols, white petroleum jelly or other known medicinal excipients. The pharmaceutical preparations can be, for example, in the form of tablets, dragees, capsules or suppositories or in a liquid form, as solutions, (for example as an elixir or syrup), suspensions or emulsions. They are optionally sterilised and/or contain auxiliaries, such as preservatives, stabilisers, wetting agents or emulsifiers, solubilising agents or salts for regulating the osmotic pressure or buffers. The pharmaceutical preparations are formulated according to customary methods.

The starting substances are known or can, if they are new, be manufactured according to methods which are in themselves known. New starting substances also form a subject of the invention.

The abovementioned compounds of the formula VIII, wherein $Z_4$ represents the -$CH_2$-W radical, and $R_1$, Ph, X and alk have the above meaning and W denotes a free hydroxyl group or a hydroxyl group esterified with a carboxylic acid, and processes for their manufacture, also form a subject of the present invention.

Lower radicals are especially those with up to 8 C atoms, and above all with up to 4 C atoms.

Aliphatic radicals are radicals whereof the free valency extends from a C atom which is not a member of an aromatic system.

Aliphatic, tricyclic or tetracyclic hydrocarbon radicals $R_1$ which can also be lower-alkylated are, for example, unsaturated and above all saturated, such as radicals of the general formula $C_mH_{(2m-y)}$, wherein m denotes the numbers 8 to 15 and y can be 5, 7, 9 or 11, such as 1- or 2-adamantyl, octahydro-1,2,4-methenopentalenyl, twistanyl or bullvalenyl.

Lower alkyl radicals are, for example, methyl, ethyl, n-propyl, isopropyl or straight or branched butyl, pentyl, hexyl, heptyl or octyl bonded in any desired position.

Alkoxy radicals are above all lower alkoxy radicals, for example methoxy, ethoxy, propoxy, isopropoxy, butoxy or amyloxy groups, and halogen atoms can be above all fluorine, chlorine or bromine atoms.

The phenylene radicals Ph are o-, m- or preferably p-phenylene radicals.

The phenylene radicals Ph can be unsubstituted or carry one, two or more substituents. Possible substituents are here, for example, the following: Alkyl radicals, such as lower alkyl radicals, especially those mentioned above, nitro groups, alkoxy radicals, halogen atoms, especially those mentioned above, or trifluoromethyl radicals.

Alkylene alk in particular has 1 to 20 C atoms and a straight chain or branched chain. A side chain which may be present is preferably in the α-position to $R_2$. Unbranched alkylene radicals with 1 to 10 C atoms, above all with 1 to 4 C atoms, and radicals which carry an unbranched alkyl radical with 1 to 8 C atoms, especially methyl, in the α-position to $R_2$, are preferred. As examples, methylene, 1,2-ethylene, 1,1-ethylene, 1,3-propylene, 1,4-butylene and 1,10-decylene may be mentioned.

Alkenylene alk in particular has 2 to 20, above all 2 to 7, C atoms and a straight chain or branched chain. A side chain which may be present is preferably in the α-position or β-position to $R_2$. Unbranched alkenylene radicals with 2 or 3 C atoms, and radicals which carry an unbranched alkyl radical with 1 to 3 C atoms in the α-position or in the β-position to $R_2$, such as vinylene, 1,3-propenylene, 1,2-propenylene, 1,2-but-1-enylene and 1,2-but-2-enylene, are preferred.

Carboxylic acids are, for example, alkanecarboxylic acids, preferably lower alkanecarboxylic acids, such as propionic acid, butyric acid and especially acetic acid, or aromatic carboxylic acids, for example benzenecarboxylic acids, which can be unsubstituted, monosubstituted or polysubstituted in the phenyl radical, possible substituents being lower alkyl, lower alkoxy, hydroxyl, trifluoromethyl and halogen, such as chlorine, bromine or iodine, or pyridinecarboxylic acids, such as 2-, 3- or 4-pyridinecarboxylic acids.

The new substances possess valuable pharmacological properties, especially an inhibiting action on the liberation of histamine, as can be shown in vitro in doses of about 0.003 to 0.015 mg/ml in the histamine liberation test on peritoneal cell suspensions of rats, using [D-Ser$^1$, Lys$^{17,18}$]-β-corticotropine-(1-19)-nonadecapeptide-tetradecyl ester-hexaacetate [R. Jaques and M. Brugger, Pharmacology 2, 361–370, (1969), M. Brugger, Helv.chim.acta, 54, 1261–1274 (1971)] and are useful as anti-allergy agents.

Furthermore they show, for example on peroral administration, in particular a hypolipidaemic activity, which can be demonstrated by standard methods from, for example, the lowering of the cholesterol level and above all of the triglyceride level in the blood after repeated administration in doses of 30 mg/kg per day to male rats. The serum lipids are extracted according to J. Folch et al [compare J. Biol. Chem. 226, 497, (1951)] and the triglycerides are determined according to G. Kessler and H. Lederer [compare Automaticen in der Analytischen Chemie (1965); Technicon GMBH, Frankfurt/Main, pages 863–972] and the total cholesterol according to W. D. Block et al, [compare ibid., pages 970–971], on an autoanalyser.

However, the new compounds are also valuable intermediate products for the manufacture of other useful substances, especially of pharmacologically active compounds.

Valuable compounds are above all those of the formula VIII, wherein $R_1$, Ph, X, alk and W have the meanings indicated above as being preferred, and especially the compounds mentioned in the examples.

The new compounds of the formula VIII can be manufactured according to methods which are in themselves known.

For example, the new compounds of the formula VIII are manufactured by reacting a compound of the formula II

   II wherein $R_1$ and Ph have the above meaning and X' represents a free hydroxyl or mercapto group, with a compound of the formula XII

   XII wherein alk and W have the above meaning and Z represents a reactive esterified hydroxyl group.

A reactive esterified hydroxyl group is in particular a hydroxyl group esterified with a strong acid, such as a strong mineral acid, especially a hydrogen halide acid, for example hydrochloric acid or above all hydrobromic acid, or sulphuric acid, or a strong organic acid, for example a sulphonic acid, such as a lower alkanesulphonic acid or benzenesulphonic acid, for example methanesulphonic acid, ethanesulphonic acid or p-toluenesulphonic acid. If the hydroxyl group W is esterified as described above, a phenol II can be employed preferably as the salt, especially as the metal salt, above all as the alkali metal salt, for example sodium salt or potassium salt. A preferred embodiment consists, for example, of reacting a suitable bromo-ester XII with the sodium salt of a corresponding phenol II. The reaction can be carried out in the usual manner, especially in an inert, preferably anhydrous solvent and/or at elevated temperature and/or in the presence of a strong base, for example an alkanolate, above all an alkali metal alkanolate, such as sodium alkanolate or potassium alkanolate, for example sodium ethanolate or sodium methanolate.

The new compounds VIII are also obtained if a compound of the formula XIII

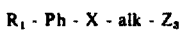   XIII wherein $R_1$, Ph, X and alk have the above meaning and $Z_3$ represents a free or functionally modified carboxyl group, is reduced.

A functionally modified carboxyl group is, for example an esterified carboxyl group, such as a lower alkoxycarbonyl group, for example methoxycarbonyl, or a halogenocarbonyl group, for example chlorocarbonyl. The reduction can be performed in the usual manner by means of a metal and an acid, for example zinc and hydrochloric acid, or a hydride, for example a simple or complex hydride, such as a borane, an aluminium hydride or a complex di-light metal hydride, for example a lower alkoxy-aluminium hydride, an alkali metal aluminium hydride, for example diborane, sodium borohydride, lithium borohydride, sodium tris-(2-dimethylaminoethoxy)-aluminium hydride or lithium aluminium hydride, in a suitable solvent, such as an ether, for example tetrahydrofurane.

In resulting compounds of the formula VIII, it is possible, within the scope of the end products, to introduce, modify or split off substituents.

Thus it is possible, in resulting compounds VIII, wherein Ph represents a substituted or unsubstituted phenylene radical, to introduce, modify or remove substituents of Ph.

Thus, products can be halogenated, such as brominated, in the customary manner, for example with free bromine, without catalysts or preferably with catalysts, such as, for example, iron-III chloride, or with N-chlorosuccinimide.

On the other hand, halogen, for example bromine, which is present can be removed hydrogenolytically, for example with hydrogen in the presence of a catalyst, such as palladium or Raney nickel or with triethyltin hydride.

Equally, nitro groups can be introduced in the usual manner, especially by nitration, for example with a mixture of nitric acid and sulphuric acid.

Furthermore, trifluoromethyl groups can be introduced into a radical Ph, for example by means of trifluoromethyl iodide in the presence of copper powder.

Resulting compounds wherein X represents sulphur can be oxidised to the S-oxides (sulphoxides) or S-dioxides (sulphones).

The oxidation to the sulphoxides or sulphones can be carried out in a manner which is in itself known, for example by reaction with a S-oxidising agent, such as hydrogen peroxide, per-acids, especially peracetic acid, perbenzoic acids or monoperphthalic acids, which can also be substituted, for example by halogen atoms, or electrolytically. In these reactions the sulphoxides are obtained at lower temperatures, especially if good cooling is used, or if only one mol equivalent of the oxidising agent is employed, whilst on warming and/or using at least 2 mol equivalents of the oxidising agent the sulphones are obtained.

Resulting S-oxides can be oxidised to the S-dioxides. This oxidation can be carried out in a manner which is in itself known, for example as in the case of the oxidation described above which leads to the dioxides.

Resulting S-oxides can be reduced to the corresponding S-unsubstituted compounds of the formula XIII, for example with a reducing agent, such as nascent hydrogen, for example zinc and mineral acid, such as hydrochloric acid, or, for example, with sulphites or hydriodic acid.

Resulting S-dioxides can be reduced to the corresponding S-unsubstituted compounds of the formula XIII, for example by reduction with a di-light metal hydride, such as lithium aluminium hydride. Here, an ether, such as dibutyl ether or tetrahydrofurane is advantageously used as the solvent.

In resulting compounds of the formula VIII, wherein W represents a free hydroxyl group or a hydroxyl group esterified with a carboxylic acid, preferably a lower alkanecarboxylic acid, for example acetic acid, an aromatic carboxylic acid such as a benzenecarboxylic acid which can be unsubstituted, monosubstituted or polysubstituted in the phenyl radical, for example benzoic acid, or a pyridinecarboxylic acid, such as 2-, 3- or 4-pyridinecarboxylic acid, for example nicotinic acid, the radicals W can be converted into one another.

Esterified hydroxyl groups, such as those mentioned above, can be saponified to free hydroxyl groups in the usual manner, for example by hydrolysis, preferably in the presence of strong bases or acids, for example sodium hydroxide solution or hydrochloric acid.

Free hydroxyl groups can be esterified in the usual manner, for example by reaction with a free lower alkanecarboxylic acid or a reactive modified lower alkanecarboxylic acid, such as a halide or anhydride, for example formic acid, acetic acid, propionic acid, acetic anhydride, ketene or acetyl chloride, or with a free or reactively modified aromatic carboxylic acid, such as a benzoic acid or a benzoyl chloride of which the phenyl radical can be unsubstituted, trisubstituted or polysubstituted, possible substituents being, for example, lower alkyl, lower alkoxy, hydroxyl, trifluoromethyl or halogen, for example, chlorine, bromine or iodine, or with a 2-, 3- or 4-pyridinecarboxylic acid, for example with nicotinic acid, advantageously in the presence of an acid, such as a mineral acid, for example sulphuric acid or hydrogen chloride, or in the presence of a water-binding agent, such as dicyclohexylcarbodiimide.

In the above reductions care must be taken, where necessary, that further reducible groups are not attacked. This care must in particular be taken in the case of the reduction with Raney nickel and hydrogen that halogen atoms which may be present and are bonded to aromatic rings are not replaced by hydrogen. Additionally, attention must be paid to a thioether grouping in all reduction reactions, especially catalytic hydrogenations. Preferably, sulphur-resistant catalysts should be used, and if necessary the hydrogen absorption should be followed volumetrically and the hydrogenation stopped after the calculated amount has been absorbed.

The reactions mentioned can optionally be carried out simultaneously or successively and in optional sequence. The reactions mentioned are carried out in the usual manner, in the presence or absence of diluents, condensation agents and/or catalysts, at lowered, ordinary or elevated temperature and if appropriate in a closed vessel.

The invention also relates to those embodiments of the process according to which a compound obtainable as an intermediate product at any stage of the process is used as the starting product and the missing process steps are carried out, or the process is stopped at any stage or a starting substance is formed under the reaction conditions or a reactant is present in the form of its salts, if appropriate.

Depending on the choice of starting substances and procedures and depending on the number of asymmetrical carbon atoms, the new compounds can be in the form of optical antipodes, racemates or isomer mixtures (for example racemate mixtures).

Resulting isomer mixtures (racemate mixtures) can be separated into the two stereoisomeric (diastereomeric) pure isomers (for example racemates) on the basis of the physicochemical differences of the constituents, in a known manner, for example by chromatography and/or fractional crystallisation.

Resulting racemates can be resolved into the optical antipodes according to known methods, for example by recrystallisation from an optically active solvent or with the aid of micro-organisms. Advantageously, the more active of the two antipodes is isolated.

The starting substances are known or can, if they are new, be manufactured according to methods which are in themselves known.

The new compounds can be used, for example, in the form of pharmaceutical preparations in which they are present as a mixture with a pharmaceutical, organic or inorganic, solid or liquid excipient suitable, for example, for enteral or parenteral administration. Possible substances for forming the excipient are those which do not react with the new compounds such as, for example, water, gelatine, lactose, starch, stearyl alcohol, magnesium stearate, talc, vegetable oils, benzyl alcohol, propylene glycols, white petroleum jelly or other known medicinal excipients. The pharmaceutical preparations can be in the form of, for example, tablets, dragees, capsules or suppositories or in a liquid form as solutions (for example as an elixir or syrup), suspensions or emulsions. They are optionally sterilised and/or contain auxiliaries, such as preservatives, stabilisers, wetting agents or emulsifiers, solubilising agents or salts for regulating the osmotic pressure or buffers. The pharmaceutical preparations are formulated according to customary methods.

The invention is described in more detail in the examples which follow.

EXAMPLE 1

13.1 g of 4-(1-adamantyl)-phenol [Stepanovetal Z. Org. chim. 8, 1619, (1970)] are added to a solution of 1.5 g of sodium in 70 ml of absolute ethanol, whilst stirring, and the mixture is evaporated to dryness in vacuo at room temperature. 50 ml of absolute benzene are then added three times and the mixture is in each case evaporated to dryness in vacuo. The evaporation residue is now suspended in 50 ml of absolute N,N-dimethylformamide and 8.0 g of propanesultone are added whilst stirring. This causes a rise in the temperature of the reaction mixture. The mixture is further stirred overnight at 80° C, with exclusion of water and is then cooled to room temperature and evaporated to dryness in vacuo at 0.1 mm Hg. The evaporation residue is suspended in ether, filtered off and well washed with ether. Repeated recrystallisation of the filter residue from a little water and ethanol yields the hygroscopic sodium salt of 4-[4-(1-adamantyl)-phenoxy]-propanesulphonic acid. The melting point is 273° C (with decomposition).

EXAMPLE 2

A suspension of 12 g of powdered potassium hydroxide and 12 g of crude 4-[4-(1-adamantyl)-phenoxy]-butyric acid nirile in 120 ml of ethylene glycol is stirred for 12 hours at 150° C in a nitrogen atmosphere. It is then allowed to cool to room temperature and the reaction mixture is partitioned between 3 times 200 ml of water and 3 times 200 ml of ethyl acetate at 0° C. The aqueous phases are acidified to pH=2 with concentrated hydrochloric acid and extracted with 3 times 200 ml of methylene chloride. The organic phases are washed until neutral, dried over sodium sulphate and evaporated in vacuo. 4-[4-(1-Adamantyl)-phenoxy]-butyric acid of melting point 169°–170° C is crystallised from the evaporation residue by means of methylene chloride/petroleum ether.

EXAMPLE 3

A solution of 4.2 g of sodium in 200 ml of absolute ethanol is mixed with 34.2 g of 4-(1-adamantyl)-phenol and stirred for 30 minutes at room temperature with exclusion of water. Thereafter, this solution is added dropwise over the course of 3 hours, whilst stirring at 50° to 60° C, to a solution of 60 g of 1,3-dibromopropane in 100 ml of absolute ethanol and stirring is continued overnight at 50° to 60° C with exclusion of water. The reaction solution is then evaporated in vacuo, 1 liter of ethanol is added to the residue and insoluble matter is filtered off. The filtrate is evaporated to dryness in vacuo, ultimately at 0.1 mm Hg, in order to remove the excess 1,3-dibromopropane. The evaporation residue contains crude 3-[4-(1-adamantyl)-phenoxy]-propyl bromide as a brown oil which is used further without additional purification.

34 g of sodium cyanide are added to a solution of 40.5 g of this crude bromide in 300 ml of absolute dimethylformamide, and the mixture is stirred for 12 hours at 60° to 70° C with exclusion of water. The reaction solution is then left to cool to room temperature and partitioned between 3 times 800 ml of water and the same quantity of methylene chloride. The organic extracts are washed until neutral, dried over sodium sulphate and evaporated in vacuo. The evaporation residue is crude 4-[4-(1-adamantyl)-phenoxy]-butyric acid nitrile.

EXAMPLE 4

100 ml of 2 N sodium hydroxide solution are added to a solution of 17 g of crude 2-[4-(1-adamantyl)-phenoxy]-propionic acid ethyl ester in 100 ml of ethanol and the mixture is stirred for 16 hours at room temperature. The reaction solution is then evaporated in vacuo to half its volume and its pH is adjusted to 2 with concentrated hydrochloric acid whilst cooling with ice. The reaction mixture is now partitioned between 200 ml of water and 3 times 200 ml of ether. The organic phases are washed until neutral, dried over sodium sulphate and evaporated in vacuo. 2-[4-(1-Adamantyl)-phenoxy]-propionic acid of melting point 140° to 150° C, which remains as the evaporation residue, is purified further by distillation. The fraction boiling at 170° to 180° C and 0.05 mm Hg contains the pure acid of melting point 159°–161° C.

EXAMPLE 5

11.5 g of 4-(1-adamantyl)-phenol are added to a solution of 1.4 g of sodium in 100 ml of absolute ethanol whilst stirring in an anhydrous atmosphere, and thereafter 13.6 g of α-bromopropionic acid ethyl ester are added under the same conditions. The mixture is then stirred for a further 24 hours at 50° C. It is now evaporated to dryness in vacuo at room temperature and the residue is partitioned between 3 times 200 ml of ether and 3 times 200 ml of 2 N sodium hydroxide solution, whilst cooling with ice. The organic phases are washed until neutral, dried over sodium sulphate and evaporated in vacuo. The evaporation residue is crude oily 2-[4-(1-adamantyl)-phenoxy]-propionic acid ethyl ester.

EXAMPLE 6

Analogously to the description in Example 5, α-bromo-decanoic acid ethyl ester and 4-(1-adamantyl)-phenol yield 2-[4-(1-adamantyl)-phenoxy]-decanoic acid ethyl ester.

EXAMPLE 7

Analogously to Example 2, 2-[4-(1-adamantyl)-phenoxy]-decanoic acid ethyl ester yields 2-[4-(1-adamantyl)-phenoxy]-decanoic acid of boiling point 220°–224° C at 0.06 mm Hg.

EXAMPLE 8

1 mol of 4-[4-(1-adamantyl)-phenoxy]-butyric acid is dissolved in excess ethanol and boiled, with addition of 3% of concentrated sulphuric acid, for 3 hours under reflux, with exclusion of moisture. The product is concentrated to half its volume and partitioned between methylene chloride and water. The organic phase is washed until neutral, dried with sodium sulphate and evaporated in vacuo to give 4-[4-(1-adamantyl)-phenoxy]-butyric acid ethyl ester of melting point 45°–46° C.

EXAMPLE 9

280 g of phosphorus pentachloride are added in portions over the course of 2 hours to a solution of 200 g of 3-oxo-hexanoic acid ethyl ester in 200 ml of absolute benzene whilst stirring at 0° C. 200 ml of water are then added dropwise with intense cooling so that the temperature never rises above 0° C. The mixture is stirred for a further 12 hours at 0° C. The organic phase is then separated off, washed with twice 100 ml of ice-cold 2 N sodium hydroxide solution and with twice 100 ml of water, dried over sodium sulphate and evaporated in vacuo. Fractional distillation of the evaporation residue gives, in the fraction boiling at 98°–102° C (20 mm), crude 3-chloro-2-hexenoic acid ethyl ester, which is used direct for further conversion.

11.4 g of 4-(1-adamantyl)-phenol and 10.4 g of the above chloro-ester give, in accordance with the method described in Example 1, a mixture of crude 3-[4-(1-adamantyl)-phenoxy]-2- and -3-hexenoic acid ethyl ester. [IR: (CO): 1,740 cm$^{-1}$ with a shoulder on the right].

EXAMPLE 10

21 ml of 1 N sodium hydroxide solution are added to a solution of a mixture of 6.8 g of crude 3-[4-(1-adamantyl)-phenoxy]-2- and -3-hexenoic acid ethyl ester in 80 ml of ethanol and the mixture is heated for 6 hours under reflux. It is then evaporated to dryness in vacuo and the evaporation residue is partitioned between 3 times 100 ml of ether and 2 times 200 ml. of water. The water phases are adjusted to pH 2 with concentrated hydrochloric acid whilst cooling with ice, and are extracted with twice 100 ml of methylene chloride. The organic phases are washed until neutral, dried over sodium sulphate and evaporated to dryness in vacuo. 3-[4-(1-Adamantyl)-phenoxy]-3-hexenoic acid of melting point 125°–127° C (decomposition) crystallises from ether-pentane.

Fractional crystallisation of the mother liquor from ether-petroleum ether gives 3-[4-(1-adamantyl)-phenoxy]-2-hexenoic acid of melting point 165°–175° C.

EXAMPLE 11

A solution of 17.5 g of 4-[4-(1-adamantyl)-phenoxy]-butyric acid chloride in as little absolute tetrahydrofurane as possible is slowly added dropwise, under anhydrous conditions and whilst stirring at −10° C, to a solution of 6.9 g of 4-pyridyl-methanol and 10.6 g of triethylamine in 100 ml of absolute tetrahydrofurane. After completion of the addition, the mixture is stirred for about 12 hours longer at about 25° C. The reaction mixture is then poured onto 200 g of ice water and extracted with twice 200 ml of ether. The organic phases are successively washed with 200 ml of saturated aqueous sodium bicarbonate solution and twice 200 ml of saturated sodium chloride solution, dried over sodium sulphate and evaporated to dryness in vacuo. The oily brown residue is chromatographed on 1 kg of silica gel with ether as the eluant. If fractions of 100 ml are taken, fractions 12–26 contain 4-[4-(1-adamantyl)-phenoxy]-butyric acid 4-pyridylmethyl ester of melting point 76°–78° C (from ether-pentane).

The starting material can be obtained as follows:

A solution of 15 g of 4-[4-(1-adamantyl)-phenoxy]-butyric acid in 150 ml of absolute benzene and 30 ml of thionyl chloride is heated with 0.3 ml of absolute dimethylformamide for 4 hours under reflux, with exclusion of water. It is then evaporated to dryness in vacuo. To remove the excess thionyl chloride completely, the residue is further evaporated with twice 200 ml of absolute benzene.

The crude oily 4-[4-(1-adamantyl)-phenoxy]-butyric acid chloride remaining in the evaporation residue is used direct, without additional purification, for further conversion.

EXAMPLE 12

A strong stream of dry ammonia is passed (for 15 minutes) into a solution of 16.5 g of 4-[4-(1-adamantyl)-phenoxy]-butyric acid chloride in 150 ml of absolute benzene under anhydrous conditions, whilst stirring. The product formed is now filtered off and washed with ether. Recrystallisation from a large amount of acetone yields pure 4-[4-(1-adamantyl)-phenoxy]-butyric acid amide of melting point 176°–177° C (needles).

EXAMPLE 13

3.22 g of N-chlorosuccinimide are added to a solution of 7 g of 4-[4-(1-adamantyl)-phenoxy]-butyric acid in 40 ml of absolute dimethylformamide whilst stirring in an anhydrous atmosphere at 0° C. The mixture is then stirred for a further 15 minutes at 0° C, 30 minutes at about 25° C and 9 hours at 50° C. The reaction solution is cooled to 0° C, filtered and treated with 40 ml of ice water. The precipitate formed is filtered off and washed with ice water. It is then recrystallised twice from ethanol. 4-[2-Chloro-4-(1-adamantyl)-phenoxy]-butyric acid of melting point 164°–166° C is thus obtained.

EXAMPLE 14

6 g of 2-(1-adamantyl)-5-methylphenol are added to a solution of 690 mg of sodium in 50 ml of absolute ethanol whilst stirring in an anhydrous atmosphere, 7.35 g of 4-bromobutyric acid ethyl ester are then added dropwise under the same conditions, and the mixture is stirred for a further 24 hours at 50° C. It is now evaporated to dryness in vacuo and the residue is partitioned between 3 times 150 ml of ether and 3 times 100 ml of water. The organic phases are dried over sodium sulphate and evaporated in vacuo, ultimately in a high vacuum so as completely to remove the excess 4-bromo-ester. 4-[2-(1-Adamantyl)-5-methyl-phenoxy]-butyric acid ethyl ester remains in the evaporation residue.

The starting material can be obtained as follows:

A mixture of 72 g of 1-bromoadamantane and 108 g of m-cresol is stirred for 90 minutes at 150° C under nitrogen. The excess m-cresol is then distilled off in vacuo. The residue is chromatographed on 1 kg of silica gel, with methylene chloride as the eluant. If fractions of 100 ml are taken, fractions 13–16 contain 2-(1-adamantyl)-5-methylphenol, which after crystallisation from petroleum ether melts at 113°–115° C.

EXAMPLE 15

A solution of 7.9 g of 4-[2-(1-adamantyl)-5-methylphenoxy]-butyric acid ethyl ester in 80 ml of ethanol and 80 ml of 1 N sodium hydroxide solution is left to stand for 60 hours at about 25° C. It is then evaporated to dryness in vacuo and the evaporation residue is partitioned between 100 ml of 2 N hydrochloric acid and twice 200 ml of ether. The organic phases are washed until neutral, treated with active charcoal, dried over sodium sulphate and evaporated in vacuo. Crystallising the evaporation residue twice from ether-petroleum ether gives 4-[2-(1-adamantyl)-5-methylphenoxy]-butyric acid of melting point 147°–150° C.

EXAMPLE 16

A mixture of 11.4 g of 4-(1-adamantyl)-phenol, 8.2 g of 3-chlorocrotonic acid ethyl ester and 60 g of anhydrous potassium carbonate in 500 ml of absolute acetone is heated for 12 hours in an anhydrous atmosphere. The mixture is then filtered hot, the residue is well rinsed with hot acetone the filtrate is evaporated to dryness in vacuo and this residue is partitioned between 3 times 200 ml of methylene chloride and 3 times 200 ml of water.

The organic phases are dried over sodium sulphate and evaporated in vacuo. Chromatography of the evaporation residue on 500 g of silica gel, with methylene chloride as the eluant, gives 3-[4-(1-adamantyl)-phenoxy]-crotonic acid ethyl ester, of melting point 97°–98° C, in fractions 5 and 6 (each of 300 ml).

EXAMPLE 17

A solution of 12.2 g of 3-[4-(1-adamantyl)-phenoxy]-crotonic acid ethyl ester in 120 ml of ethanol and 24 ml of 2 N sodium hydroxide solution is stirred for 5 days at about 25° C. It is then evaporated in vacuo to a volume of approx. 20 ml and the residue is partitioned between twice 200 ml of methylene chloride and 200 ml of 2 N hydrochloric acid. The organic phases are washed until neutral, treated with active charcoal, dried over sodium sulphate and evaporated in vacuo. Crystallisation of the evaporation residue from ethanol gives 3-[4-(1-adamantyl)-phenoxy]-crotonic acid of melting point 215°–218° C (decomposition).

EXAMPLE 18

Analogously to the method described in Example 16, the use of ethyl bromoacetate and p-(1-adamantyl)-phenol as starting materials gives 4-(1-adamantyl)-phenoxyacetic acid ethyl ester of melting point 89°–90° C (flakes; from etherpentane).

EXAMPLE 19

4-(1-Adamantyl)-phenoxyacetic acid ethyl ester gives, analogously to Example 17, 4-(1-adamantyl)-phenoxyacetic acid of melting point 185°–187° C (from ether/petroleum ether).

EXAMPLE 20

Analogously to the method described in Example 5, the use of p-(1-adamantyl)-phenol and 4-bromobutyric acid ethyl ester as starting materials gives 4-4-(1-adamantyl)-phenoxy-butyric acid ethyl ester of boiling point 150° C (0.03 mm).

EXAMPLE 21

Analogously to the procedure described in Example 5, the use of 5-chloro-pentanecarboxylic acid ethyl ester and p-(1-adamantyl)-phenol as starting materials gives 5-[4-(1-adamantyl)-phenoxy]-pentanecarboxylic acid ethyl ester of boiling point 170°–180° C (0.05 mm).

EXAMPLE 22

Starting from 5-[4-(1-adamantyl)-phenoxy]-pentane-carboxylic acid ethyl ester, 5-[4-(1-adamantyl)-phenoxy]-pentanoic acid of melting point 163°–165° C (from chloroform/petroleum ether) is obtained analogously to Example 17.

EXAMPLE 23

120 ml of fuming nitric acid in 40 ml of glacial acetic acid are added dropwise to a solution of 31.4 g of 4-[4-(1-adamantyl)-phenoxy]-butyric acid in 100 ml of glacial acetic acid and 30 ml of methylene chloride at −5° C, whilst stirring in an anhydrous atmosphere. After completion of the addition, the mixture is stirred for a further 15 minutes at −5° C and 30 minutes at −3° C. The reaction mixture is then poured onto 1 kg of ice and extracted with 3 times 200 ml of methylene chloride. The organic phases are washed until neutral, dried over sodium sulphate and evaporated in vacuo. Chromatography of the evaporation residue on 1 kg of silica gel, with ethyl acetate as the eluant, gives 4-[2-nitro-4-(1-adamantyl)-phenoxy]-butyric acid of melting point 182°–185° C (from methylene chloride/petroleum ether) and 4-[2,6-dinitro-4-(1-adamantyl)-phenoxy]-butyric acid of melting point 170°–172° C (from ethanol-pentane).

EXAMPLE 24

Starting from 1,10-dibromodecane and p- (1-adamantyl)-phenol and sodium cyanide, 11-[4-(1-adamantyl)-phenoxy]-undecanoic acid of melting point 87°–91° C (from ether/petroleum ether/pentane) is obtained via the nitrile, analogously to Example 3 and 2.

EXAMPLE 25

12 g of the trifluoroacetic acid salt of 3-pyridyltrifluoroacetate are added to a solution of 10 g of 4-[2-(1-adamantyl)-phenoxy]-butyric acid in 50 ml of anhydrous pyridine whilst stirring in an anhydrous atmosphere and the mixture is stirred for about 16 hours at about 25° C. The reaction solution is then poured into 500 g of ice water and the precipitate formed is filtered off. The filter residue is washed with water and dissolved in 300 ml of ether. The ether solution is successively washed with 200 ml of water, 200 ml of saturated sodium bicarbonate solution and 300 ml of water, dried over sodium sulphate and evaporated to dryness in vacuo. 4-[4-(1-Adamantyl)-phenoxy]-butyric acid 3-pyridyl ester of melting point 88°–89° C crystallises from ether-hexane.

EXAMPLE 26

A solution of 1.45 g of sodium nitrite in 6 ml of water is added dropwise to a suspension of 5.3 g of p-(1-adamantyl)-aniline hydrochloride in 10 ml of concentrated hydrochloric acid and 30 ml of water at 0° C, whilst stirring.

The mixture is stirred for a further 2 hours at 0° C. The solution which has now cooled to 0° C and is homogeneous is added dropwise at 4° C, whilst stirring, to a solution which is obtained by dissolving 5.05 g of sodium sulphide enneahydrate and 660 mg of sulphur in 5.7 ml of water and 5 g of sodium hydroxide in 20 ml of water with heating.

After completion of the addition, the reaction mixture is allowed to rise to about 25° C, stirred for 1 hour at about 25° C and then heated for 15 minutes to 60° C. It is then cooled to 0° C, adjusted to pH 2 with concentrated hydrochloric acid and extracted with 3 times 100 ml of methylene chloride. The organic phases are washed until neutral, dried over sodium sulphate and evaporated in vacuo. The crude and oxidation-sensitive 4-(1-adamantyl)-thiophenol contained in the evaporation residue (brown oil) is immediately converted further, without additional purification.

A solution of 5 g of the crude 4-(1-adamantyl)-thiophenol obtained above, in 25 ml of absolute ethanol and 25 ml of absolute tetrahydrofurane is added dropwise to a solution of 500 mg of sodium in 20 ml of absolute ethanol whilst stirring in a dry nitrogen atmosphere, and 2.9 ml of 4-bromobutyric acid ethyl ester are then added under the same conditions. After completion of the addition, the mixture is heated to 50° C for 14 hours. It is then evaporated to dryness in vacuo and the evaporation residue is partitioned between 3 times 100 ml of methylene chloride and 100 ml of 2 N hydrochloric acid. The organic phases are washed until neutral, dried over sodium sulphate and evaporated in vacuo. Chromatography of the evaporation residue on 240 g of silica gel, with benzene as the eluant, yields chromatographically pure 4-[4-(1-adamantyl)-phenylthio]-butyric acid ethyl ester in the form of a yellow-brown oil (IR spectrum: C=O band at 1,740 cm$^{-1}$ (in $CH_2Cl_2$)).

100 ml of 2 N sodium hydroxide solution are added to a solution of 6 g of crude 4-[4-(1-adamantyl)-phenylthio]-butyric acid ethyl ester in 300 ml of ethanol and 100 ml of tetrahydrofurane and the mixture is left to stand for 3 days at about 25° C with exclusion of air. The reaction solution is then evaporated in vacuo to a volume of about 100 ml and partitioned between 3 times 200 ml of methylene chloride and 200 ml of 2 N hydrochloric acid. The organic phases are washed until neutral, dried over sodium sulphate and evaporated in vacuo. Crystallisation of the evaporation residue from benzene/petroleum ether gives 4-[4-(1-adamantyl)-phenylthio]-butyric acid of melting point 136°–138° C.

EXAMPLE 27

Analogously to the procedure described in Example 5, the use of 11.4 g of 4-(1-adamantyl)-phenol and 14.5 g of 4-bromocrotonic acid ethyl ester as starting materials gives 4-[4-(1-adamantyl)-phenoxy]-crotonic acid ethyl ester of melting point 91–93° C (from methanol).

EXAMPLE 28

Analogously to the procedure described in Example 4, starting from 7.3 g of 4-[4-(1-adamantyl)-phenoxy]-crotonic acid ethyl ester and saponifying with sodium hydroxide solution gives a mixture of 4-[4-(1-adamantyl)-phenoxy]-2-butenoic acid and 4-[4-(1 adamantyl)-phenoxy]-3-butenoic acid of melting point 195°–199° C (from chloroform-pentane).

EXAMPLE 29

A solution of 0.9 g of the mixture of 4-[4-(1-adamantyl)-phenoxy]-2-butenoic acid and 4-[4-(1-adamantyl)-phenoxy]-3-butenoic acid in 30 ml of absolute methanol is hydrogenated with 0.3 g of palladium (5% strength on charcoal) until 1 equivalent of hydrogen has been taken up (normal pressure, about 25° C). The catalyst is then filtered off, and the filtrate is mixed with 10 ml of 2 N sodium hydroxide solution and left to stand for 24 hours at about 25° C. It is then evaporated in vacuo to half its volume. The evaporation residue is partitioned between 50 ml of 2 N hydrochloric acid and 3 times 50 ml of methylene chloride. The organic phases are washed until neutral, dried over sodium sulphate and evaporated in vacuo. Crystallisation of the evaporation residue from ethanol gives 4-[4-(1-adamantyl)-phenoxy]-butyric acid of melting point 170°–172° C.

EXAMPLE 30

52.6 g of p-bromophenyl benzyl ether in 100 ml of absolute tetrahydrofurane are added dropwise to 5 g of magnesium filings, covered with a little absolute tetrahydrofurane, whilst stirring at 40° C in an anhydrous atmosphere, the speed of addition being such that the temperature never exceeds 50° C. After completion of the addition, the mixture is heated for 2 hours under reflux. The reaction solution is then cooled to 20° C and decomposed dropwise with a solution of 27 g of 2-adamantanone in 100 ml of absolute tetrahydrofurane. After completion of the addition, the mixture is heated for 2 hours under reflux and is then stirred for about 12 hours at about 25° C. It is then evaporated to half its volume in vacuo, poured onto a mixture of 500 g of ice and 500 ml of saturated ammonium chloride solution and extracted with 3 times 500 ml of ether. The organic phases are washed with twice 500 ml of water, dried over sodium sulphate and evaporated to dryness in vacuo. Crystallisation of the evaporation residue from ether/petroleum ether gives 4-(2-hydroxy-2-adamantyl)-phenyl-benzyl ether of melting point 119°–121° C.

A solution of 19.5 g of 4-(2-hydroxy-2-adamantyl)-phenyl-benzyl ether in 200 ml of glacial acetic acid is hydrogenated with 2 g of palladium on charcoal at about 25° C, under normal pressure, until 2 equivalents of hydrogen have been taken up. The catalyst is then filtered off and the filtrate is evaporated to dryness in vacuo. Crystallisation of the evaporation residue from ether/petroleum ether gives 4-(2-adamantyl)-phenol of melting point 180°–181° C.

7.0 g of this phenol are converted by means of 9.05 g of 4-bromo-butyric acid ethyl ester, in accordance with the procedure described in Example 5, into 4-[4-(2-adamantyl)-phenoxy]-butyric acid ethyl ester, which after chromatographic purification on 260 g of silica gel, with methylene chloride as the migrating agent, is obtained as a chromatographically pure, oily compound.

EXAMPLE 31

A solution of 7.2 g of 4-[4-(2-adamantyl)-phenoxy]-butyric acid ethyl ester in 150 ml of ethanol is mixed with 150 ml of sodium hydroxide solution and the mixture is left to stand for 24 hours at 30° C. The reaction solution is then evaporated by dryness in vacuo and the evaporation residue is partitioned between 100 ml of 2

N hydrochloric acid and twice 100 ml of ether. The organic phases are washed until neutral, dried over sodium sulphate and evaporated to dryness in vacuo. Recrystallisation of the evaporation residue from ethanol gives 4-[4-(2-adamantyl)-phenoxy]-butyric acid of melting point 163°–165° C.

EXAMPLE 32

0.5 g of palladium (5% strength on charcoal) is added to a solution of 4.0 g of 4-[2-nitro-4-(1-adamantyl)-phenoxy]-butyric acid in 200 ml of 5 N methanolic hydrochloric acid amd the acid is hydrogenated at about 25° C under normal pressure until 3 equivalents of hydrogen have been taken up. The catalyst is then filtered off and the filtrate is evaporated in vacuo to a volume of 50 ml and left to stand for 2 days at about 25° C. The reaction solution is then partitioned between 3 times 100 ml of methylene chloride and 200 ml of saturated sodium bicarbonate solution. The organic phases are washed with water until neutral, dried over sodium sulphate and evaporated in vacuo. Crystallisation of the evaporation residue from ether/petroleum ether gives 4-[4-(1-adamantyl)-2-aminophenoxy]-butyric acid methyl ester of melting point 97°–98° C.

EXAMPLE 33

1.00 g of sodium nitrite in 5 ml of water is added dropwise, whilst stirring, to a suspension of 5 g of 4-[4-(1-adamantyl)-2-amino-phenoxy]-butyric acid methyl ester in 10 ml of concentrated hydrochloric acid and 30 ml of water. After completion of the addition, the mixture is stirred for a further 3 hours at 0° C. The reaction solution is then filtered cold. The filtrate, kept at 0° C, is then added in portions to a solution of 5 g of freshly prepared copper-(I) chloride in 20 ml of concentrated hydrochloric acid at 0° C, whilst stirring. After completion of the addition, the temperature is allowed to rise to about 25° C and the mixture is then heated on a water bath until the evolution of nitrogen has ceased. It is then filtered, the residue is well rinsed with methylene chloride, and the filtrate is partitioned between 3 times 50 ml of methylene chloride and 50 ml of water. The organic phases are combined and evaporated in vacuo. The evaporation residue is dissolved in 100 ml of ethanol and 20 ml of 2 N sodium hydroxide solution and the mixture is left to stand for 24 hours at about 25° C. It is then evaporated to dryness in vacuo and the evaporation residue is partitioned between 150 ml of 2 N hydrochloric acid and twice 50 ml of methylene chloride. The organic phases are washed until neutral, dried over sodium sulphate and evaporated in vacuo. Chromatography of the evaporation residue on 100 g of silica gel, with ether as the migrating agent, and subsequent crystallisation from ethanol, gives 4-[4-(1-adamantyl)-2-chlorophenoxy]-butyric acid of melting point 164°–166° C.

EXAMPLE 34

A 10% strength solution of 4-[4-(1-adamantyl)-phenoxy]-butyric acid ethyl ester in dioxane is slowly added dropwise to a suspension of 1.1 equivalents of lithium aluminium hydride in a little dioxane, whilst stirring and excluding moisture.

After completion of the addition, the mixture is stirred for a further 10 hours at 50° C.

The mixture is then cooled to 0° C and the excess lithium aluminium hydride is destroyed by dropwise addition of water under a protective atmosphere of nitrogen, whilst stirring.

The reaction mixture is partitioned between 2 N hydrochloric acid and methylene chloride and the organic phase is separated off, washed until neutral, dried with sodium sulphate and evaporated in vacuo.

4-[4-(1-Adamantyl)-phenoxy]-butanol which has an absorption band in the IR at 3,600 cm$^{-1}$ and melts at 98°–99° C, remains as the residue.

EXAMPLE 35

13 g of nicotinic acid chloride hydrochloride are added in portions to a solution of 14.6 g of 4-[4-(1-adamantyl)-phenoxy]-butanol in 180 ml of absolute pyridine and 90 ml of absolute benzene whilst stirring at 5° C in an anhydrous atmosphere, and 40 ml of triethylamine are then added under the same conditions. The cooling bath is then removed and the mixture is stirred for a further 2 days at about 25° C. The reaction solution is now partitioned between 2 litres of ice water and 3 times 200 ml of methylene chloride. The organic phases are then washed with 6 times 800 ml of water, dried over sodium sulphate and evaporated to dryness in vacuo. Crystallisation of the evaporation residue from ether/petroleum ether after treatment with active charcoal gives 4-[4-(1-adamantyl)-phenoxy]-butyl-nicotinate of melting point 83°–84° C.

EXAMPLE 36

Analogously to the method described in Example 35, the use of 14.6 g of 4-[4-(1-adamantyl)-phenoxy]-butanol and 13.0 g of isonicotinic acid chloride hydrochloride as starting materials gives 4-[4-(1-adamantyl)-phenoxy]-butylisonicotinate of melting point 92°–93° C.

EXAMPLE 37

22.8 g of p-(1-adamantyl)-phenol are added to a solution of 2.8 g of sodium in 200 ml of absolute ethanol whilst stirring in an anhydrous atmosphere and 14.2 g of 3-chloropropanol are then added dropwise under the same conditions. After completion of the addition, the mixture is stirred for a further 24 hours at 60° C. It is then evaporated to dryness in vacuo, the residue is dissolved in ether, the solution is filtered and the filtrate is evaporated to dryness in vacuo. Chromatography of the evaporation residue on 1 kg of silica gel with ethyl acetate as the eluant gives 3-[4-(1-adamantyl)-phenoxy]-propanol-(1) of melting point 98°–100° C (from methanol-water).

EXAMPLE 38

Tablets containing 10 mg of active substance can be produced to have, for example, the following composition:

| Composition | |
|---|---|
| 4-[4-(1-Adamantyl)-phenoxy]-butyric acid | 10.0 mg |
| Wheat starch | 29.5 mg |
| Lactose | 50.0 mg |
| Colloidal silica | 5.0 mg |
| Talc | 5.0 mg |
| Magnesium stearate | 0.5 mg |
| | 100.0 mg |

Manufacture

The 4-[4-(1-adamantyl)-phenoxy]-butyric acid is mixed with a part of the wheat starch, with lactose and with colloidal silica and the mixture is forced through a sieve. A further part of the wheat starch is worked into a paste with a 5-fold amount of water on a water bath and the powder mixture is kneaded with this paste until a slightly plastic mass has been produced.

The plastic mass is forced through a sieve of approx. 3 mm mesh width and dried and the dry granules are again forced through a sieve. Thereafter, the remaining wheat starch, the talc and the magnesium stearate are mixed in and the resulting mixture is pressed to give tablets weighing 100 mg.

We claim:

1. A compound of the formula

wherein $R_1$ is unsubstituted adamantyl, Ph is unsubstituted phenylene, or phenylene substituted by nitro, lower alkyl, lower alkoxy, halogeno or trifluoromethyl, X is thio, sulphinyl or sulphonyl, alk is alkylene with up to 10 carbon atoms which may be branched in the α-position with respect to $R_2$, or alkenylene with up to 7 atoms the double bond of which extends from the carbon atom in α- or β-position to $R_2$, and which may be branched in the β-position with respect to $R_2$, and $R_2$ is carboxyl, lower alkoxycarbonyl, pyridyloxycarbonyl, pyridylcarbonyloxy or pyridylmethoxycarbonyl, or a therapeutically acceptable salt thereof.

2. A compound as claimed in claim 1, wherein $R_1$ is unsubstituted adamantyl, Ph is 1,4-phenylene, X is thio, alk is $-(CH_2)_n-CH(R_3)-$, wherein n is 0, 1 or 2 and $R_3$ is hydrogen or straight-chain alkyl with 1 to 8 C atoms, and $R_2$ is carboxyl, methoxycarbonyl, ethoxycarbonyl or pyridylmethoxycarbonyl, or a therapeutically acceptable salt thereof.

3. A compound as claimed in claim 1, wherein $R_1$ is unsubstituted adamantyl, Ph is 1,2- or 1,4-phenylene which are optionally substituted by nitro, methoxy, methyl or chlorine, X is thio, alk is unbranched alkylene with 1 to 4 C atoms which can carry unbranched alkyl with 1 to 8 C atoms in the α-position to $R_2$, or is unbranched alkenylene with 2 or 3 C atoms which can carry unbranched alkyl with 1 to 3 C atoms in the α-position or β-position to $R_2$, and $R_2$ is carboxyl, $C_1$-$C_4$-alkoxycarbonyl, pyridyloxycarbonyl, pyridylmethoxycarbonyl, or a therapeutically acceptable salt thereof.

4. A compound as claimed in claim 1, wherein $R_1$ is unsubstituted adamantyl, Ph is 1,4-phenylene, X is thio, alk is unbranched alkylene with 1 to 4 C atoms or is unbranched alkenylene with 2 or 3 C atoms and $R_2$ is carboxyl, $C_1$-$C_3$-alkoxycarbonyl, pyridyloxycarbonyl or pyridylmethoxycarbonyl, or a therapeutically acceptable salt thereof.

5. A compound as claimed in claim 1 being 4-[4-(1-adamantyl)-phenylthio]-butyric acid ethyl ester.

6. A compound as claimed in claim 1 being 4-[4-(1adamantyl)-phenylthio]-butyric acid or a therapeutically acceptable salt thereof.